United States Patent
Brown

(10) Patent No.: US 8,496,631 B2
(45) Date of Patent: Jul. 30, 2013

(54) APPARATUS AND METHOD FOR INCREASING FLOW RESISTANCE AROUND A PROBE

(76) Inventor: David C. Brown, Fort Myers, FL (US)

( * ) Notice: Subject to any disclaimer, the term of this patent is extended or adjusted under 35 U.S.C. 154(b) by 1751 days.

(21) Appl. No.: 11/174,935

(22) Filed: Jul. 5, 2005

(65) Prior Publication Data

US 2007/0073213 A1    Mar. 29, 2007

(51) Int. Cl.
- *A61M 5/00* (2006.01)
- *A61M 31/00* (2006.01)
- *A61M 37/00* (2006.01)
- *A61M 25/00* (2006.01)

(52) U.S. Cl.
USPC ......... 604/264; 604/93.01; 604/523; 604/524

(58) Field of Classification Search
USPC ............... 604/163, 22, 264, 506, 158, 161, 604/93.01, 164.01, 164.02, 164.08, 171, 604/48, 164.09, 164.1, 164.11, 523, 524, 604/525; 606/107
See application file for complete search history.

(56) References Cited

U.S. PATENT DOCUMENTS

| | | | |
|---|---|---|---|
| 3,788,326 A * | 1/1974 | Jacobs | 128/207.15 |
| 4,504,268 A * | 3/1985 | Herlitze | 604/170.01 |
| 4,696,308 A * | 9/1987 | Meller et al. | 600/567 |
| 4,808,154 A * | 2/1989 | Freeman | 604/22 |
| 5,282,786 A * | 2/1994 | Ureche | 604/22 |
| 5,354,265 A * | 10/1994 | Mackool | 604/22 |
| 5,403,323 A * | 4/1995 | Smith | 606/107 |
| 5,456,662 A * | 10/1995 | Edwards et al. | 604/22 |
| 5,718,676 A * | 2/1998 | Barrett | 604/22 |
| 6,033,376 A * | 3/2000 | Rockley | 604/22 |
| 6,299,591 B1 * | 10/2001 | Banko | 604/22 |
| 6,605,093 B1 * | 8/2003 | Blake | 606/107 |
| 6,685,694 B2 * | 2/2004 | Finch et al. | 604/508 |
| 6,733,479 B1 * | 5/2004 | Ott | 604/264 |
| 2002/0072754 A1 | 6/2002 | Camerlengo | 606/107 |
| 2003/0208218 A1 | 11/2003 | Kadziauskas et al. | 606/169 |
| 2004/0068300 A1 | 4/2004 | Kadziauskas et al. | 607/3 |

OTHER PUBLICATIONS

Brochure entitled "COHRlastic Silicone Rubber Products" and "Foam Tapes," dated 2004, Saint-Gobain.
Microincision Cataract Surgery (MICS) and MISC Lenses, Jorge L. Alio, MD, PhD. (Spain).
"USPTO Search", Hits 1 thru 6, Search Terms: phacoemulsification and bimanual, Jun. 2, 2005.

* cited by examiner

*Primary Examiner* — Kevin C Sirmons
*Assistant Examiner* — Shefali Patel
(74) *Attorney, Agent, or Firm* — John J. Love; Claude Cooke, Jr.; Cooke Law Firm

(57) ABSTRACT

An apparatus is provided for decreasing or eliminating flow of fluid between a probe and an incision during surgical procedures. The apparatus may comprise a deformable layer on the probe. The deformable layer may be comprised of a polymer foam, which may be covered with a surface layer. In another embodiment, baffles on a base layer are provided. The deformable layer or baffles may be on a slidable base surrounding the probe.

4 Claims, 5 Drawing Sheets

APPARATUS AND METHOD FOR INCREASING FLOW RESISTANCE AROUND A PROBE

BACKGROUND OF INVENTION

1. Field of the Invention

This invention pertains to decreasing flow around a probe, cannula, needle or trocar, such as during aspiration and irrigation of fluids within a closed volume for medical purposes. More particularly, apparatus and method are provided for minimizing or eliminating fluid flow around a phacoemulsification probe or other instrument during irrigation and aspiration of the eye or human organs or cavities.

2. Description of Related Art

Traditional small incision cataract surgery uses a coaxial irrigation-aspiration system and ultrasound to fragment the cataract material. Recently, Micro-Incision Cataract Surgery (MICS) has evolved, which uses two very small incisions and divides the irrigation mode from the ultrasound-aspiration mode of the phacoemulsification technique, thus introducing "bimanual" phacoemulsification. The advantage of MICS is smaller incisions in the eye, which are less invasive, allow quicker healing and typically leave less astigmatism. In the bi-manual technique the surgeon uses both hands during the phacoemulsification procedure, with separate irrigation and aspiration instruments.

New ultrasound and other fragmenting machines have also increased the appeal of MICS and allowed smaller, tighter incisions with less chance of "wound burn" by reducing the amount of energy employed inside the eye, using techniques such as described in US 2004/0068300, for example. Similarly, vitreous resection has also progressed by the utilization of smaller incisions and bi-manual removal of vitreous. The small vitrectomy tip normally involves use of a hollow shaft enclosing a rotating or isolating blade to which an aspiration line is affixed.

In both instances, cataract lens or vitreous removal, the infusion needle and the mechanically active aspirator needle used in the bi-manual technique are preferably "water tight" in the incision of the eye, so as to form a closed fluid system. Working in a closed environment provides a significant improvement from routine cataract surgery, where the closed chamber concept is not available. There is a need to optimize the probes to allow the balance between outflow and inflow in this new environment. The goal is to have a pressurized volume of fluid in the anterior chamber, posterior chamber or vitreous body of an eye and to minimize the outflow and inflow volumes. The decrease in flow rate into and out of the eye can reduce the circulation inside the eye and lead to greater safety and control of the surgery.

New micro instruments have been designed to be incorporated into the system used by the surgeon in MICS. The new probes may be of smaller size and are designed to be used without an irrigation sleeve. They should be designed to be manipulated efficiently through the micro-incisions without creating enough tension in the corneal tissue to tear the incision or damage the tissue. Friction between the probe and the corneal tissue should preferably be minimized.

It is important to avoid thermal burn when using MICS. Some prior methods depended on cooling the phaco tip and incision tissue by leaking solution through the incision. Newer methods reduce tip temperature by operating in a pulse mode or computer-controlled mode as described in US 2004/0068300, which minimizes the amount of energy input to the ultrasound probe and lowers its temperature, which may decrease the need for leaking through the incision. A Teflon coated tip has also been used in the past, which provides lower friction between the probe and the tissue and adds a thermal insulation layer to the probe.

What is needed is apparatus and method to increase resistance to fluid flow or to provide a limited seal around a phacoemulsification probe or other needle, cannula or trocar through an incision to minimize or prevent fluid leakage or to afford a closed system at normal pressures for performing surgery. The apparatus should also assist in avoiding thermal damage to tissue.

SUMMARY OF THE INVENTION

A device is provided for increasing flow resistance around a probe during surgical procedures. In one embodiment, the device includes a deformable polymer foam layer around the probe. The foam layer may have a low friction layer on top and be shaped for easy insertion into an incision. In another embodiment, the device includes baffles on a base layer. The baffles are selected to deform as a probe moves through an incision. In yet another embodiment, the deformable layer is attached to a slidable base. A method for selecting a deformable layer is provided.

DETAILED DESCRIPTION

Figure 1:
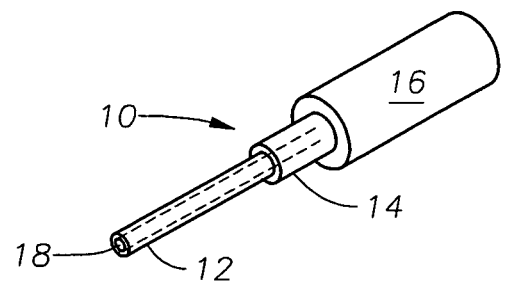
FIG. 1 is an isometric drawing of a prior art phacoemulsification probe designed for use with an infusion sleeve to provide coaxial irrigation and evacuation.

Referring to FIG. 1, prior art phacoemulsification probe 10 is shown. The probe includes needle 12, shoulder section 14 and ultrasonic source 16. Phacoemulsification needle 12 is used to emulsify the nucleus of a cataract in the natural lens of the eye. A sleeve (not shown) may be placed over section 14 to carry water between the sleeve and needle 12. Water serves to act as a coolant of the needle to decrease danger of burning of the cornea. Lumen 18 through needle 12 allows suction to be placed in the opening to aspirate fluids from the eye along with fragments of cataract to be removed. The sleeve (not shown) over needle 12 serves to prevent corneal burn. The diameter of the sleeve over needle 12 is selected by the surgeon to fit inside an incision in the cornea and to allow, in some instances, leakage through the incision to assist in cooling of the needle.

When the newer bi-manual phacoemulsification method is used, two incisions are made and irrigation and aspiration are separately carried out through separate incisions. No sleeve on the phacoemulsification probes for both infusion and aspiration is necessary in such instances. Infusion fluid may pass through lumen 18 in a needle such as shown in FIG. 1 and ultrasonic source 16 may not be present.

Figure 2:
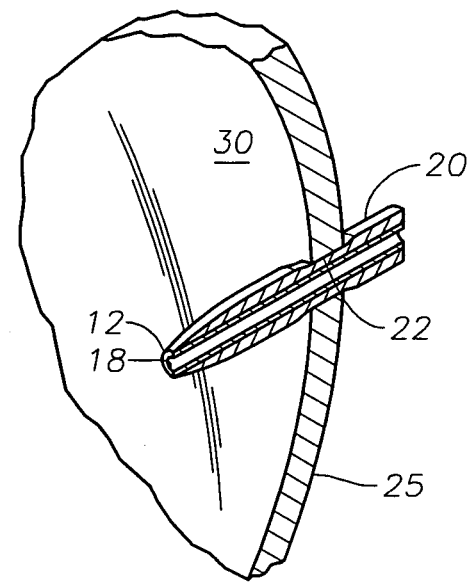
FIG. 2 is an isometric drawing of one embodiment of the apparatus disclosed herein with a deformable cover on a phacoemulsification probe.

Referring to FIG. 2, probe or cannula 12, containing lumen 18, is covered with deformable material 20. Cannula 12 and deformable material 20 have been placed through incision 22 in cornea 25 and into anterior chamber 30 of an eye. The outside diameters of probe 12 and deformable material 20 are selected in view of the size of incision 22 so as to cause material 20 to be deformed to fit inside incision 22 as it passes through the incision without placing excess stress on cornea 25 around incision 22. Preferably, deformable material 20 will exert enough force against incision 22 to allow only very low flow rate between material 20 and incision 22 when pressure inside an eye is within the normal range of eye pressure, which is up to about 30 mm Hg, or about 0.6 psi. Tests may be performed in simulated incisions using different material properties and thicknesses of deformable material 20 to select the material and thickness on probe 12 so as to allow material 20 to substantially seal against incision 22 or at least greatly increase resistance to fluid flow through incision 22 when pressure in chamber 30 is within the normal range. Material 20 may also be selected to allow flow through incision 22 at a higher rate should pressure in chamber 30 increase to a value that could cause damage to an eye.

Deformable material 20 is preferably a foamed polymeric material having a selected compression modulus. The foamed material may be an open-cell foam or a closed-cell foam. If material 20 is a closed-cell foam, deformable material 20 may form a hydraulic seal between needle 12 and cornea 25 because flow does not occur through the body of the foam. If material 20 is an open-cell material, it may allow some fluid flow between needle 12 and cornea 25, but it may greatly increase the resistance to flow through incision 22 in cornea 25. The thickness of the layer of deformable material 20 and the compression modulus of the material may be selected to allow material 20 to seal against incision 22 as probe 12 is moved through incision 22.

Figure 3:
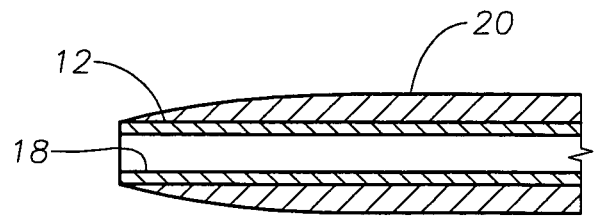
FIG. 3 is a cross-section view of one embodiment of the apparatus disclosed herein.
Figure 4:
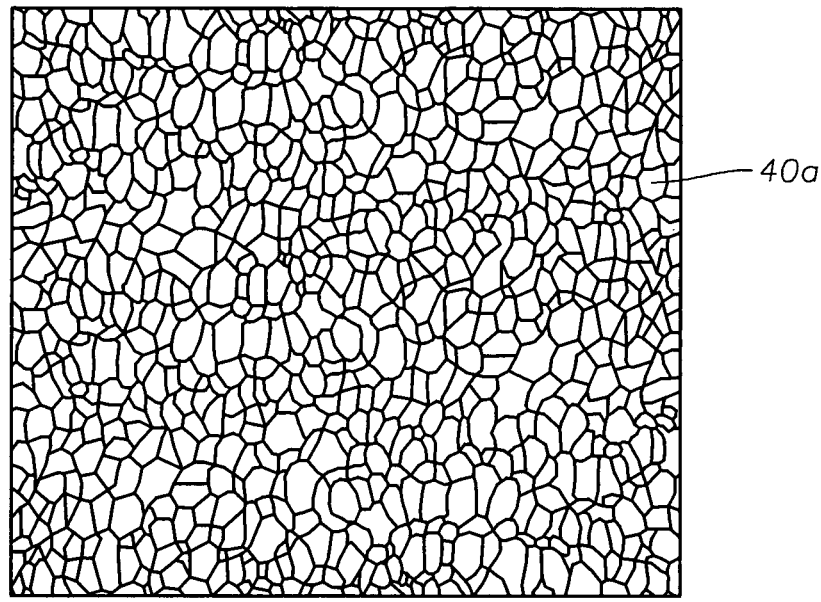
FIG. 4 is a drawing of a closed-cell elastomeric foam.
Figure 5:
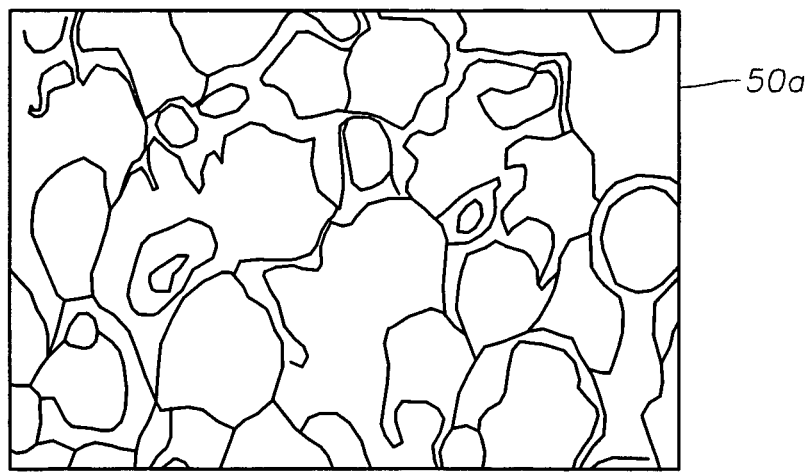
FIG. 5 is a drawing of an open-cell elastomeric foam.

A cross-sectional view of needle, cannula or probe 12 with lumen 18 and deformable material 20 is shown in FIG. 3. Preferably, deformable material 20 has lesser thickness on the distal end of needle 12 such that it will more easily enter an incision. Material 20 is preferably a polymeric material selected for its inertness, its deformability, its permeability to fluid and its thermal conductivity. A suitable material is a silicone rubber product. Other rubber-like or elastic materials may be used. A particular suitable material is silicone elastic material available from Saint-Gobain Performance Plastics of Grandville, N.Y. The material is available in either closed-cell foam, open-cell foam or solid. A closed-cell foam is illustrated in FIG. 4 and an open-cell (or partially open-cell) foam is illustrated in FIG. 5.

Figure 6A:
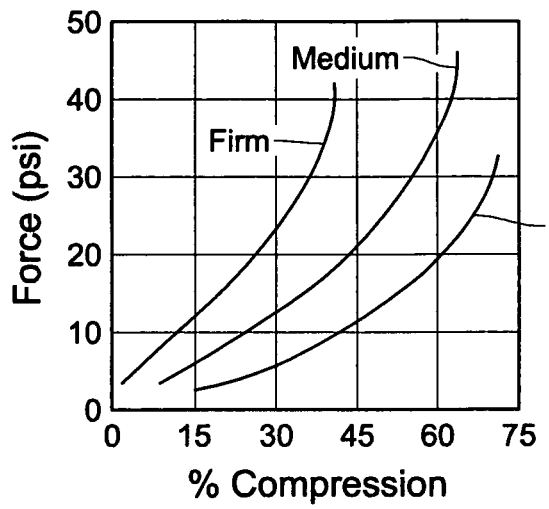
FIGS. 6A, 6B and 6C are plots of force vs compression for various materials.
Figure 6B:
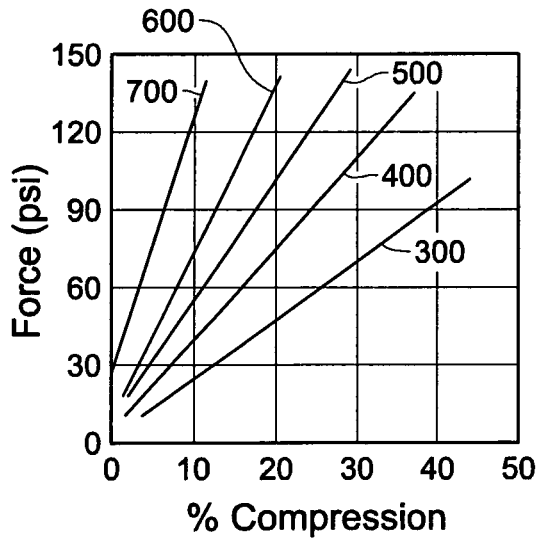
Figure 6C:
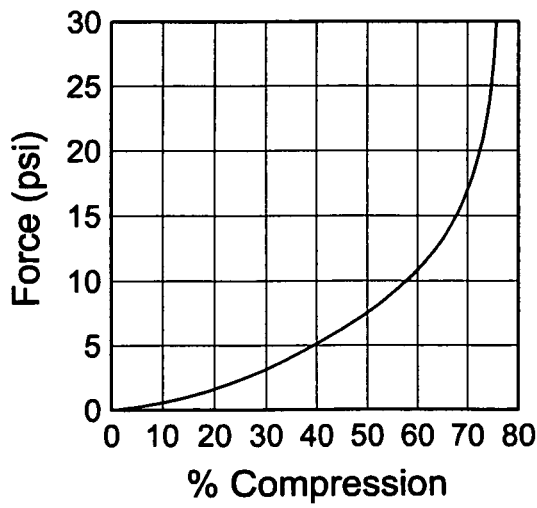

The compression modulus of the Saint-Gobain materials is illustrated in FIGS. 6A, 6B and 6C. In FIG. 6A, the force required to cause compression is shown for firm, medium and soft silicone sponge rubber materials. In FIG. 6C similar data are shown for a silicone foam rubber material, which is the most deformable material illustrated. FIG. 6B shows compression data for five different compositions of solid silicone rubber, which illustrates the much higher force required to obtain compression of solid material and demonstrates that a more deformable material must be used to avoid excessive physical force to corneal tissue. Data for the most deformable material, shown in FIG. 6C, shows that a force of 1.5 lbs. per square inch (psi) results in a compression of the material of about 20 percent, which translates into an effective compression modulus of 13.3 percent compression per psi at this pressure. In contrast, the most deformable material illustrated in FIG. 6B shows a compression modulus of 20/47=0.42 percent compression per psi.

Figure 7:
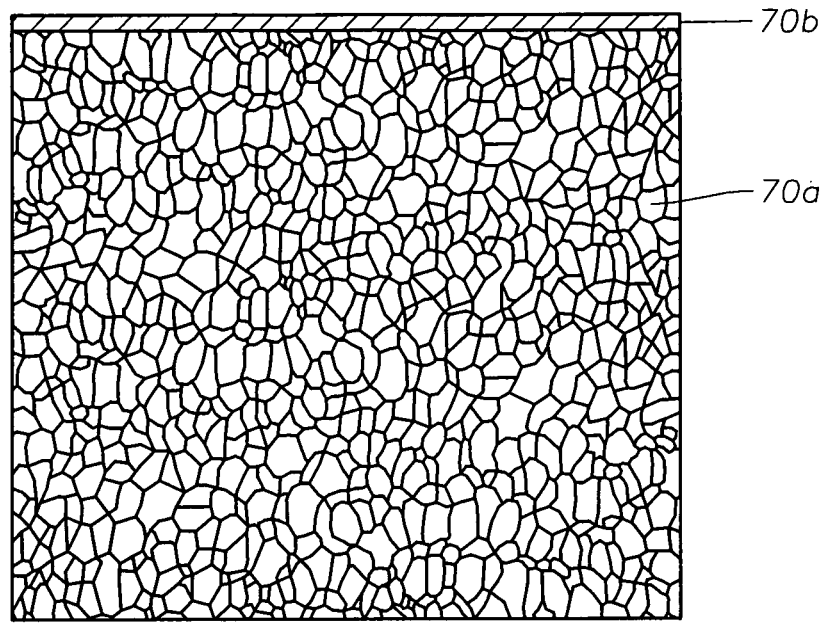
FIG. 7 is a drawing of a film on the surface of a closed-cell elastomeric foam.

Saint-Gobain Performance Plastics also supplies a variety of tapes made of foamed materials. The tapes may be supplied with coatings or adhesives on the surfaces. Such foamed polymer having a smooth surface layer may be manufactured and used as deformable material 20. Such a configuration is illustrated in FIG. 7, for a closed cell material. Closed-cell foam 70a is covered with layer 70b, which is preferably made of a material, such as TEFLON, having low frictional resistance as the coated deformable material on a needle is moved through an incision in a cornea of an eye. If the foam is open cell, the coating may be perforated to allow fluid to flow through the coating as the deformable material deforms by moving through an incision.

Figure 8:
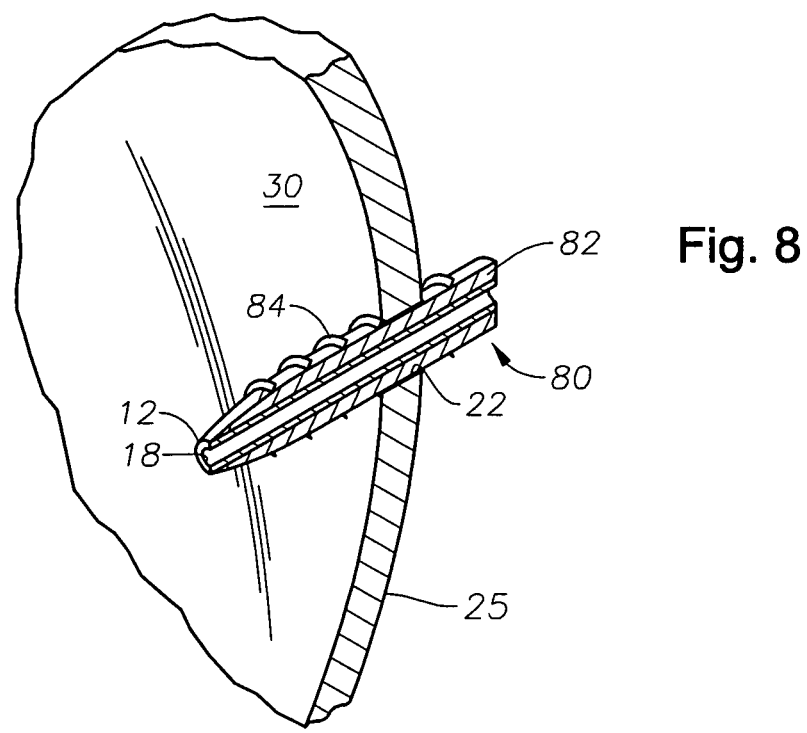
FIG. 8 is an isometric drawing of one embodiment of the apparatus disclosed herein with a baffle structure to decrease flow around a phacoemulsification probe.

FIG. 8 illustrates an alternate method of obtaining a deformable covering on needle 12. Deformable coating 80 is made up of base 82 and circumferential baffles 84. Base 82 and baffles 84 are preferably constructed of a deformable elastomeric material and are sized such that deformable coating 80 may pass through incision 22 in cornea or sclera 25. Baffles 84 may be made convex toward anterior chamber 30 or concave toward anterior chamber 30 or perpendicular to base 82. Baffles 84 are designed so as to increase resistance to flow from chamber 30. FIG. 8 shows one baffle 84 confined by incision 22 to lie against base 82, but base 82 may be smaller in size than incision 22, such that baffle 84 may be extended to contact cornea 25 or to extend in incision 22 toward cornea 25. A suitable elastomeric material for base 82 and baffles 84 is a silicone rubber. The modulus of the rubber may be varied in base 82 and baffles 84 to provide a selected low leakage rate at a selected pressure in anterior chamber 30.

Figure 9:
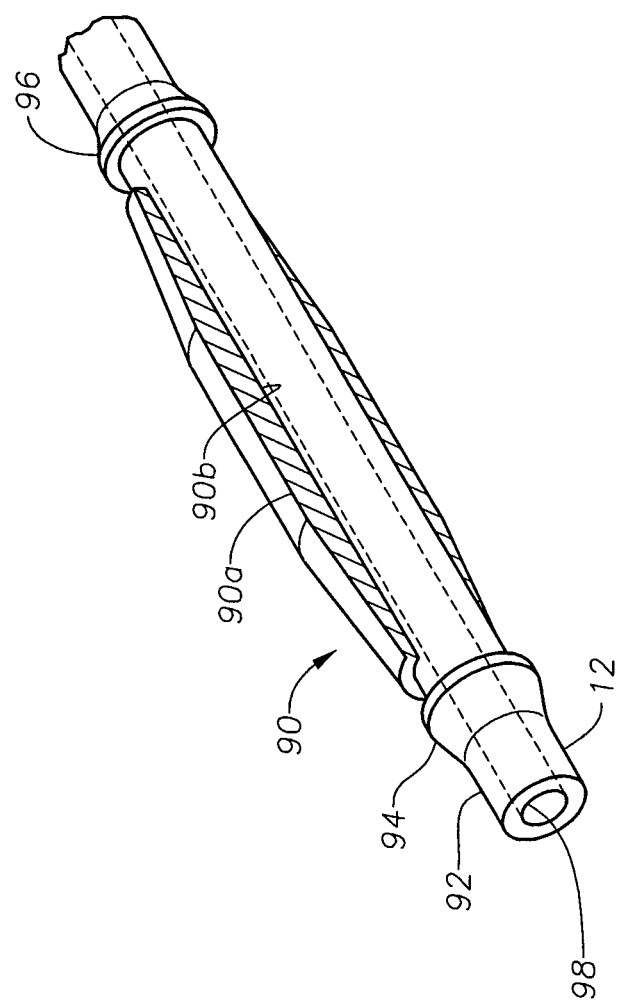
FIG. 9 is an isometric drawing of one embodiment of the apparatus disclosed herein with a deformable cover on a slidable base disposed between stops on a phacoemulsification probe.

FIG. 9 illustrates deformable sleeve 90 that consists of deformable material 90a that is attached to rigid base 90b. Base 90b is sized to slide along needle 92 containing lumen 98. Stops 94 and 96 at selected locations on needle 92 keep sleeve 90 constrained along a segment of needle 92 and allow manipulation of needle 92 for phacoemulsification procedures or other surgical procedures while sealing or increasing resistance to flow between needle or probe 92 and an incision (not shown). The same materials may be used for material 90a as discussed above referring to FIG. 2. Base 90b may be formed from TEFLON or other plastic material.

Other benefits of deformable material 20 in FIGS. 2 and 3 and material 90a in FIG. 9 are as a barrier to heat flow from probe 12 and to isolate vibration of probe 12 from an incision. This can be of particular benefit when probe 12 is vibrated for phacoemulsification purposes.

Although bi-manual phacoemulsification has been used to illustrate application of a phacoemulsification probe having a deformable coating, it should be understood that the deformable material and methods described herein may be used to create a tamponade to prevent or minimize leakage of fluid around a needle, trocar or cannula used in other medical procedures.

To use the apparatus disclosed herein in eye surgery, the surgeon forms an incision of small size through the wall of the eye (cornea or sclera). Multiple incisions may also be used, in the event of removing tissue, such as lens material or vitreous, as well as portions of the iris, trabecular meshwork or other structures. Additionally the instruments may be modified to implant into the eye, including medication, lenses, retinal and sub-retinal implants.

Although the present disclosure has been described in certain details, it should be understood that various changes, substitutions and alterations can be made thereto without departing from the scope and spirit of the invention, which is defined by the appended claims.

What I claim is:

1. An apparatus for increasing resistance to fluid flow between a probe and an incision, comprising:
   the probe having an outer cylindrical surface,
   a deformable layer comprising a hollow cylindrical sleeve having an inside surface surrounding the probe, the deformable layer having a length along the probe and a thickness selected to increase the resistance to fluid flow between the probe and the incision at a selected distance along the length and being formed of a material having a selected compression modulus, and the inside surface of the sleeve being in continuous contact with the outer surface of the probe,
   a surface layer on the deformable layer, and
   wherein the surface layer further contains perforations.

2. The apparatus of claim 1 wherein the selected compression modulus is greater than 0.42 percent per psi.

3. The apparatus of 1 wherein the deformable layer is comprised of a polymer sponge or foam.

4. The apparatus of claim 3 wherein the polymer sponge or foam is a silicone.

* * * * *